US007750186B2

(12) United States Patent
Jörges et al.

(10) Patent No.: US 7,750,186 B2
(45) Date of Patent: Jul. 6, 2010

(54) METHODS FOR THE MANUFACTURE OF BIPHENYL AMINES

(75) Inventors: Wolfgang Jörges, Odenthal (DE); Jens-Dietmar Heinrich, Burscheid (DE); Reinhard Lantzsch, Wuppertal (DE)

(73) Assignee: Bayer CropScience AG, Monheim (DE)

( * ) Notice: Subject to any disclaimer, the term of this patent is extended or adjusted under 35 U.S.C. 154(b) by 653 days.

(21) Appl. No.: 11/574,088

(22) PCT Filed: Aug. 13, 2005

(86) PCT No.: PCT/EP2005/008838

§ 371 (c)(1),
(2), (4) Date: Jul. 19, 2007

(87) PCT Pub. No.: WO2006/024388

PCT Pub. Date: Mar. 9, 2006

(65) Prior Publication Data

US 2008/0194835 A1    Aug. 14, 2008

(30) Foreign Application Priority Data

Aug. 27, 2004   (DE)   ........................ 10 2004 041 531

(51) Int. Cl.
    *C07C 211/45*   (2006.01)
(52) U.S. Cl. ..................................................... 564/305
(58) Field of Classification Search ................. 564/305
    See application file for complete search history.

(56) References Cited

U.S. PATENT DOCUMENTS

| 3,547,917 | A  | 12/1970 | Kulka et al. |
| 5,330,995 | A  | 7/1994  | Eicken et al. |
| 5,416,103 | A  | 5/1995  | Eicken et al. |
| 5,438,070 | A  | 8/1995  | Eicken et al. |
| 7,098,227 | B2 | 8/2006  | Dunkel et al. |
| 7,388,097 | B2 | 6/2008  | Elbe et al. |
| 2005/0124815 | A1 | 6/2005 | Elbe et al. |
| 2005/0143428 | A1 | 6/2005 | Dunkel et al. |

FOREIGN PATENT DOCUMENTS

| EP | 0 545 099 A2 | 6/1993 |
| EP | 0 589 301 A1 | 3/1994 |
| EP | 0 589 313 A1 | 3/1994 |
| WO | WO 01/42223 A1 | 6/2001 |
| WO | WO 02/064562 A1 | 8/2002 |
| WO | WO 03/066609 A1 | 8/2003 |
| WO | WO 03/066610 A1 | 8/2003 |
| WO | WO 03/069995 A1 | 8/2003 |
| WO | WO 03/070705 A1 | 8/2003 |

OTHER PUBLICATIONS

Arcadi, A., et al., "Palladium-Catalyzed Hydrovinylation of Vinyl Triflates with Alkynes: An Approach to the Synthesis of 3-Vinylfuran-2(5H)-ones," *Eur. J. Org. Chem.* 1999:3305-3313, Wiley-VCH Verlag GmbH (1999).

Bluestone, H., et al., "Chlorinated Derivatives of Butadiene Sulfone and Diels-Alder Reactions of 3,4-Dichlorothiophene 1,1-Dioxide," *J. Org. Chem.* 26:346-351, American Chemical Society (1961).

Dmowski, W., et al.,"3-Chloro-4-fluorothiophene-1,1-dioxide. A new synthetically useful fluorodiene," *J. Fluor. Chem.* 88:143-151, Elsevier Science S.A. (1998).

Fernandes, M.A. and Reid, D.H., "Synthesis of 3,1-Benzothiazines by Cyclisation of 2-Thioformylaminodiphenylacetylenes," *Synlett.* 14:2231-2233, Georg Thieme Verlag Stuttgart (2003).

Feuerstein, M., et al., "Coupling reactions of aryl bromides with 1-alkynols catalysed by a tetraphosphine/palladium catalyst," *Tetrahedron Lett.* 45:1603-1606, Elsevier Ltd. (Feb. 2004).

Gribble, G.W., "Recent developments in indole ring synthesis—methodology and applications," *J. Chem. Soc., Perkin Trans. 1*:1045-1075, The Royal Society of Chemistry (2000).

Hong, K.B., et al., "Synthesis of 2-substituted indoles by palladium-catalyzed heteroannulation with Pd-NaY zeolite catalysts," *Tetrahedron Lett.* 45:693-697, Elsevier Ltd. (Jan. 2004).

Huber, W.F., et al., "Vinyl Aromatic Compounds. II. *o*-, *m*- and *p*-Vinylbiphenyls," *J. Am. Chem. Soc.* 68:1109-1112, American Chemical Society (1946).

Jeong, N., et al., "A Facile Preparation of the Fluoroaryl Zinc Halides: an Application to the Synthesis of Diflunisal," *Bull. Korean Chem. Soc.* 21:165-166, Korean Chemical Society (2000).

Koradin, C., et al., "Synthesis of polyfunctional indoles and related heterocycles mediated by cesium and potassium bases," *Tetrahedron* 59:1571-1587, Elsevier Science Ltd. (2003).

Lehmler, H.-J., et al., "Synthesis of Polychlorinated Biphenyls (PCBs) and Their Metabolites Using the Suzuki-Coupling," in *PCBs*, Robertson, L.W. and Hanson, L.G., eds., The University Press of Kentucky, Lexington, KY, pp. 57-60 (2001).

Lu, Y., et al., "Bond Alteration in Azulenes," *J. Am. Chem. Soc.* 122:2440-2445, American Chemical Society (2000).

Mahanty, J.S., et al. ,"Palladium-catalyzed Heteroannulation with Acetylenic Carbinols as Synthons-Synthesis of Quinolines and 2,3-Dihydro-4(1H)-quinolones," *Tetrahedron* 53:13397-13418, Elsevier Science Ltd. (1997).

Quang, N.N., et al., "Orientation dans la Réaction de Friedel-Crafts D'acétylation des Bromofluorobenzénes," *Recueil* 83:1142-1148, Sociétéchimique neerlandaise (1964).

Wommack, J.B., et al., "The Synthesis of Quinoline- and Isoquinolinecarboxaldehydes," *J. Het. Chem.* 6:243-245, Elsevier B.V. (1969).

International Search Report for International Application No. PCT/EP2005/008838, European Patent Office, Netherlands, mailed on Feb. 9, 2006.

(Continued)

*Primary Examiner*—Golam M Shameem
(74) *Attorney, Agent, or Firm*—Sterne, Kessler, Goldstein & Fox P.L.L.C.

(57) ABSTRACT

The present invention relates to a new method for the manufacture of substituted biphenyl amines, new intermediate products and their manufacture, as well as a method for the manufacture of fungicidally active carboxamides.

3 Claims, No Drawings

METHODS FOR THE MANUFACTURE OF BIPHENYL AMINES

This application is a National Stage of International Application No. PCT/EP2005/008838, filed Aug. 13, 2005, which claims the benefit of German Patent Application No. 102004041531.5, filed Aug. 27, 2004. The entirety of each of these applications is incorporated by reference herein.

The present invention relates to a new method for the manufacture of substituted biphenyl amines, new intermediate products and their manufacture, as well as a method for the manufacture of fungicidally active carboxamides.

It is already known that biphenyl derivates can be prepared from phenyl boronic acids and phenyl halogenides using Suzuki coupling or Stille coupling (see e.g. WO 01/42223, WO 02/064562, WO 03/070705, Robertson and Hansen (eds.) *PCBs*, The University Press of Kentucky 2001, 57-60).

It is further known that biphenyl derivatives can be obtained by reacting aryl zinc halogenides with aryl halogenides (Bull. Korean Chem. Soc. 2000, 21, 165-166).

The disadvantage of these methods is the high manufacturing costs. The manufacture of a boronic acid requires a Grignard reaction, and the transition metal catalysed cross-coupling (e.g. according to Suzuki) requires relatively high quantities of palladium catalysts or (Bull. Korean Chem. Soc. 2000, 21, 165-166) the use of nearly equivalent quantities of zinc, which must be disposed of as waste, and the carcinogenic substance, dibromomethane, is necessary for activation of the zinc.

A particular disadvantage is that self-coupling of the boronic acids cannot be avoided (Robertson and Hansen (eds.) *PCBs*, The University Press of Kentucky 2001, 57-60) and there is the danger that polychlorinated biphenyls (PCB's) can form (see the following reaction diagram).

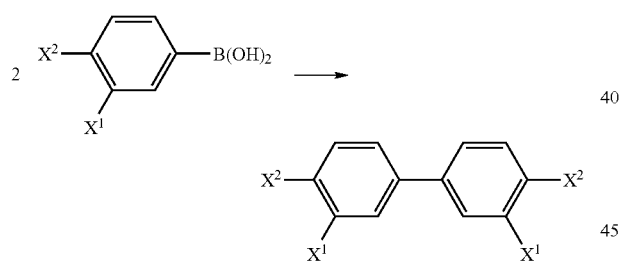

In the method according to the invention, however, the second phenyl ring is constructed via a Diels-Alder reaction.

Thus, the object of the present invention was to devise a novel, economical method for obtaining the biphenyl amine at a simultaneous higher total yield and increased purity.

Therefore, the subject of the present invention is a method for the manufacture of biphenyl amines of the general Formula (I)

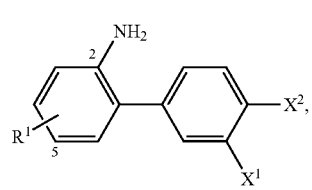

where
$R^1$ stands for hydrogen, fluorine, chlorine, $C_1$-$C_4$-alkyl, $C_1$-$C_4$-alkoxy, $C_1$-$C_4$-alkylthio or $C_1$-$C_4$-halogenalkyl,
$X^1$ stands for fluorine, chlorine or bromine,
$X^2$ stands for fluorine, chlorine or bromine, characterised in that, according to Method A,
(1) in a first step, anilides of Formula (II)

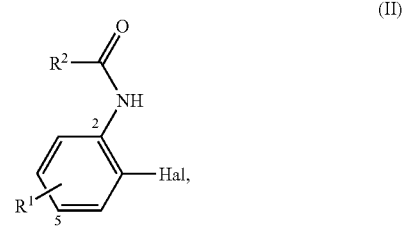

where
Hal stands for chlorine, bromine or iodine,
$R^2$ stands for hydrogen, $C_1$-$C_4$-alkyl or $C_1$-$C_4$-alkoxy, and
$R^1$ has the meanings specified above,
are reacted with 2-methylbut-3-yn-2-ol of Formula (III)

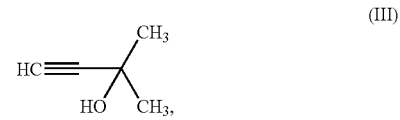

(2) in a second step, acetone is separated from the thus obtained alkynyl anilides of Formula (IV)

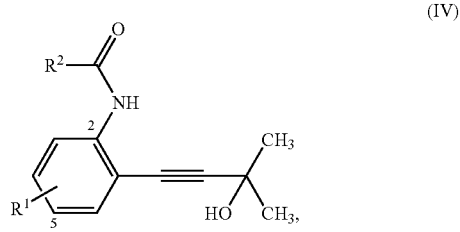

where $R^1$ and $R^2$ have the meanings specified above,
in the presence of bases,
(3) in a third step, the thus obtained ethynyl anilides of Formula (V)

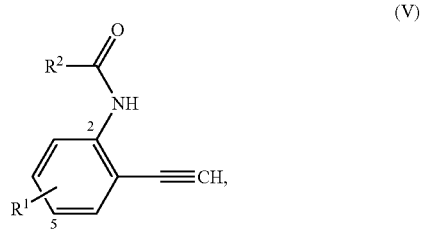

where $R^1$ and $R^2$ have the meanings specified above, are reacted with thiophene dioxides of Formula (VI)

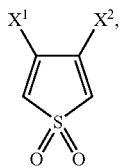

(VI)

where $X^1$ and $X^2$ have the meanings specified above, and (4) in a fourth step, the protective group [—C(=O)R²] on the nitrogen is separated from the thus obtained biphenyl amides of Formula (VII)

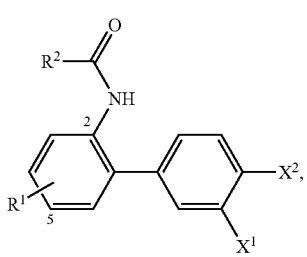

(VII)

where $R^1$, $R^2$, $X^1$ and $X^2$ have the meanings specified above, under acidic or basic conditions.

Surprisingly, by using this reaction sequence, the biphenyl amines of Formula (I) can be produced with good yields from inexpensive initial substances without a Grignard reaction. The transition metal catalysed coupling with butinol only requires very small amounts of the catalyst, which are less than the amounts necessary for a Suzuki coupling.

If N-(2-bromo-4-fluorophenyl)acetamide, 2-methylbut-3-yn-2-ol and 3,4-dichlorothiophene-1,1-dioxide are used as initial compounds, all four steps of Method A according to the invention can be illustrated by the following reaction diagram:

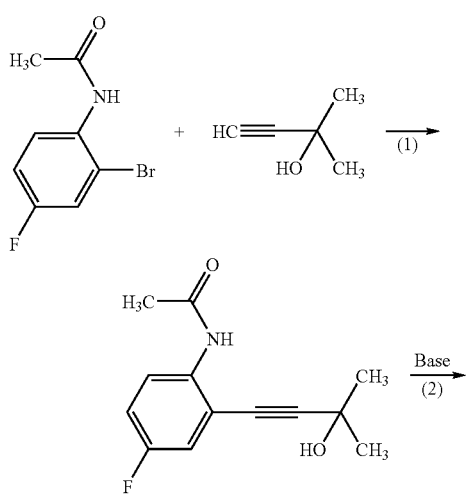

-continued

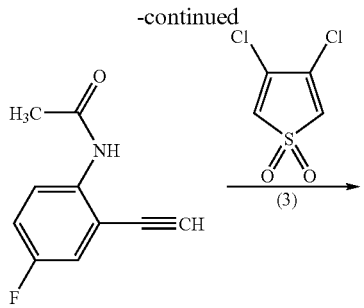

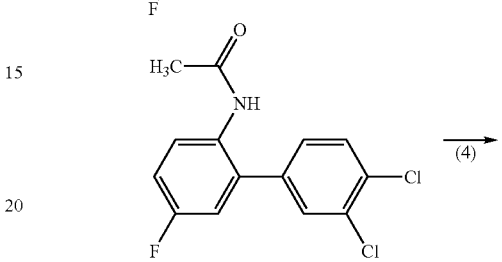

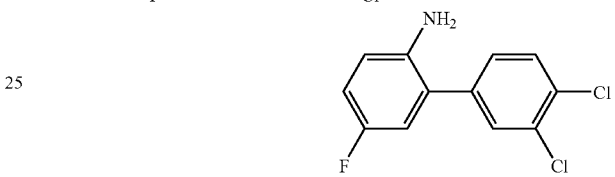

Method A according to the invention is preferably carried out while using initial compounds, in which the indicated moieties each have the following meanings. The preferred, particularly preferred and quite particularly preferred meanings apply to all compounds, in which the respective moieties occur.

Hal preferably stands for chlorine.
Hal further preferably stands for bromine.
Hal further preferably stands for iodine.
Hal particularly preferably stands for bromine.
$R^1$ preferably stands for hydrogen.
$R^1$ further preferably stands for fluorine, whereby fluorine particularly preferably is located in the 3-, 4- or 5-position, quite particularly preferably in the 3- or 5-position, p in the 5-position of the respective compound [see e.g. Formula (I)].
$R^1$ further preferably stands for chlorine, whereby chlorine particularly preferably is located in the 3- or 5-position of the respective compound.
$R^1$ further preferably stands for methyl or iso-propyl, whereby methyl or iso-propyl particularly preferably is located in the 6-position of the respective compound.
$R^1$ further preferably stands for trifluoromethyl, whereby trifluoromethyl particularly preferably is located in the 4- or 5-position of the respective compound.
$R^1$ further preferably stands for methoxy or methylthio, whereby methoxy or methylthio particularly preferably is located in the 4-, 5- or 6-position of the respective compound.
$R^2$ preferably stands for hydrogen, methyl, ethyl, iso-propyl, tert-butyl, methoxy, ethoxy, iso-propoxy or tert-butoxy.
$R^2$ particularly preferably stands for methyl, tert-butyl, methoxy or tert-butoxy.
$R^2$ quite particularly preferably stands for methyl.
$X^1$ preferably stands for fluorine.
$X^1$ further preferably stands for chlorine.
$X^1$ further preferably stands for bromine.

$X^2$ preferably stands for fluorine.
$X^2$ further preferably stands for chlorine.
$X^2$ further preferably stands for bromine.

Preferably, Method A according to the invention yields biphenyl amines of Formula (I-a)

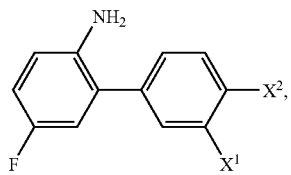

(I-a)

where $X^1$ and $X^2$ have the meanings specified above.

For this purpose, anilides of Formula (II-a)

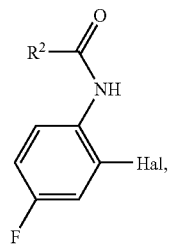

(II-a)

where Hal and $R^2$ have the meanings specified above, are employed as initial compounds.

The anilides of Formula (II), which are to be used as initial compounds when carrying out the first step of Method A according to the invention are partially known or can be obtained according to known methods [see e.g. Synlett, 2003, (14), 2231; Recl. Trav. Chim. Pay-Bas. 1964, 83, 1142; J. Het. Chem. 1969, 6, 243].

The 2-methylbut-3-yn-2-ol of Formula (III), which is to be additionally used as an initial compound when carrying out the first step of Method A according to the invention, is known and commercially available.

The alkynyl anilides of Formula (IV), which are to be used as initial compounds when carrying out the second step of Method A according to the invention, are novel and are a further subject of this patent application. Alkynyl anilides of Formula (IV) are obtained from the first step of Method A according to the invention.

The ethynyl anilides of Formula (V), which are to be used as initial compounds when carrying out the third step of Method A according to the invention, are partially novel (if $R^1$ stands for fluorine) and are also a subject of this patent application. Ethynyl anilides of Formula (V) are obtained from the second step of Method A according to the invention.

The thiophene dioxides of Formula (VI), which are to be used as initial compounds when carrying out the third step of Method A according to the invention, are known (see e.g. J. Org. Chem. 1961, 26, 346-351; J. Fluorine Chem. 1998, 88, 143-151; J. Amer. Chem. Soc. 2000, 122, 2440-2445).

Explanatory Notes on the Individual Reaction Steps:

First Step

The coupling of aryl halogenides with acetylene is principally known. In the present case, however, it is problematic to obtain the compounds with good yields, since various secondary reactions can occur. The first secondary reaction is the dehydration of alkynyl anilides of Formula (IV), after which it is no longer possible to separate acetone to form ethynyl anilides of Formula (V) (see the following reaction diagram).

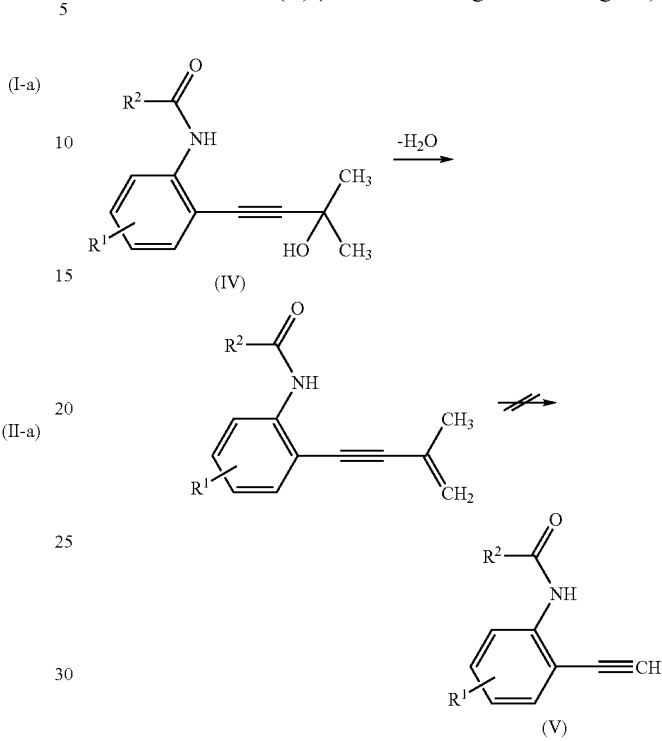

It is actually known, that butinols only react with aryl halogenides at extremely moderate yields for this reason (see e.g. Tetrahedron Lett. 2004, 45, 1603-1606).

The second secondary reaction is the formation of indoles according to the following reaction diagram:

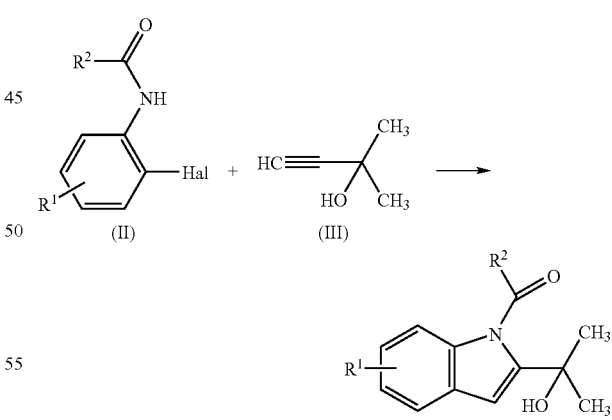

This cyclisation reaction from 2-halogen anilides and acetylenes is also known from literature (see e.g. Tetrahedron Lett. 2004, 45, 693-697).

The first step of Method A according to the invention is performed in the presence of a transition metal catalyst, preferably in the presence of dichlorobis(triphenylphosphine) palladium (II). However, other catalysts can be used as well, such as e.g. tetrakis(triphenylphosphane)palladium (0).

The first step of Method A according to the invention is preferably performed in the presence of copper halides and triphenylphosphine as co-catalysts, whereby copper iodide is particularly preferred.

The first step of Method A according to the invention can principally be performed without copper salts as well, whereby the amount of palladium catalyst is significantly increased.

When performing the first step of Method A according to the invention, the work is done in the presence of a base, preferably in the presence of secondary or tertiary amines. The following are preferably used: diethylamine, dipropylamine, dibutylamine, piperidine, triethylamine, tripropylamine, tributylamine, particularly preferably triethylamine.

When performing the first step of Method A according to the invention, the use of a diluent is not necessary. However, alkali carbonates can be used as a base, e.g. in nitrites, as a solvent.

When performing the first step of Method A according to the invention, the work is generally done at temperatures in the range from 20° C. to 120° C., preferably in the range from 50° C. to 100° C.

When performing the first step of Method A according to the invention, in general between 1 Mol and 1.5 Mol, preferably between 1 Mol and 1.1 Mol 2-methylbut-3-yn-2-ol of Formula (III) as well as between 0.01 and 1 molar percent of transition metal catalyst and 1 to 10 Mol of a base are used per 1 Mol of anilide of Formula (II).

Surprisingly, it was found that, in contrast to the customary necessary quantities of the transition metal catalyst, the reaction according to the invention occurs at very good yields even when very low quantities of the catalyst are utilised.

Second Step

The second step of Method A according to the invention is preferably performed in a diluent, which boils at a higher temperature than acetone, so that acetone can be continuously removed from the reaction mixture, under reduced pressure if applicable.

All solvents that are inert with respect to bases come into consideration such as hydrocarbons, chlorohydrocarbons, ethers or amides. The following are preferably used: cyclohexane, toluene, xylene, chlorobenzene, 1,2-dimethoxyethane, dioxane, dimethylformamide, dimethylacetamide, N-methylpyrrolidinone, while toluene and xylene are particularly preferred.

The second step of Method A according to the invention is performed in the presence of bases. The following come into consideration as bases: alkali metal hydroxides, such as e.g. sodium hydroxide, potassium hydroxide; alcoholates, such as e.g. sodium methylate, sodium ethylate, sodium butylate; carbonates, such as sodium carbonate, potassium carbonate.

An indole ring closure cannot be fully avoided, since this is also a base-catalysed reaction (see e.g. Tetrahedron 2003, 59, 1571; J. Chem. Soc. Perkin Trans. 1, 2000, 1045-1075). However, the indole formation can nevertheless be suppressed to a large extent with quick cooling following completion of the reaction.

When performing the second step of Method A according to the invention, the work is generally done at temperatures between 40° C. and 150° C. The selected temperature is as low as possible, however high enough that the reaction occurs sufficiently quickly.

When performing the second step of Method A according to the invention, generally between 0.05 Mol and 1.0 Mol of base is used per 1 Mol of alkynyl anilide of Formula (IV).

Third Step

The third step of Method A preferably occurs in the presence of a solvent at increased temperatures.

When performing the third step of Method A according to the invention, the following come into consideration as solvents: hydrocarbons, chlorohydrocarbons, nitrites, alcohols, ketones, ethers, amides or esters. The following are specifically mentioned: toluene, xylene, mesitylene, decalin, chlorobenzene, dichlorobenzene, butyronitrile, valeronitrile, propionitrile, cyclohexanone, ethyleneglycol monoethylether, anisole, dimethylformamide, acetic acid butyl ester. The following are preferably used: xylene, butyronitrile or valeronitrile.

When performing the third step of Method A according to the invention, the work is generally done at temperatures between 80° C. and 200° C.

In order to minimise the dimerisation of thiophene dioxides of Formula (VI), an ethynyl anilide of Formula (V) is preferably placed in a solvent and a thiophene dioxide of Formula (VI) is added slowly at an increased temperature.

In order to attain a complete reaction, an excess of the thiophene dioxide of Formula (VI) is employed. However, it is possible to use less than the specified amount as well. Normally, 0.9 Mol to 1.5 Mol, preferably 1.05 Mol to 1.25 Mol, of thiophene dioxide of Formula (VI) is used per Mol of ethynyl anilide of Formula (V). It is also possible to use 0.5 Mol to 1.5 Mol, preferably 0.9 Mol to 1.25 Mol, of thiophene dioxide of Formula (VI) per Mol of ethynyl anilide of Formula (V). Purification occurs through crystallisation.

Fourth Step

Separation of the [—C(═O)R²] protective group on the nitrogen can occur in either basic or acidic conditions according to known methods (see e.g. T. W. Greene, P. G. M. Wuts, Protective Groups in Organic Synthesis, Ed. 3, New York, Wiley & Sons, 1999).

All steps of Method A according to the invention, if not otherwise indicated, are generally performed under normal pressure. However, it is also possible to work under increased or decreased pressure.

The biphenyl amines of Formula (I) are valuable intermediate products for the manufacture of fungicidally active compounds.

Thus, fungicidally-active carboxamides (see WO 03/070705) of Formula (VIII)

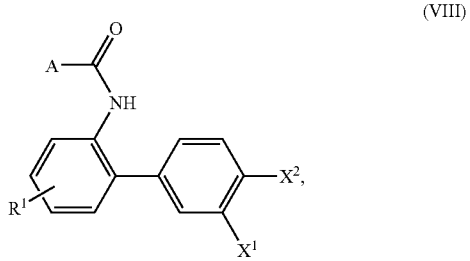

(VIII)

where

R¹ stands for hydrogen, fluorine, chlorine, $C_1$-$C_4$-alkyl, $C_1$-$C_4$-alkoxy, $C_1$-$C_4$-alkylthio or $C_1$-$C_4$-halogenalkyl, X¹ stands for fluorine, chlorine or bromine, X² stands for fluorine, chlorine or bromine, A stands for one of the following moieties, A1 to A7:

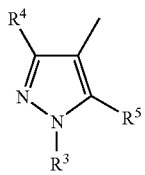
A1

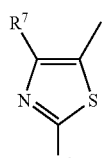
A2

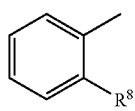
A3

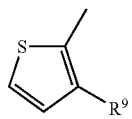
A4

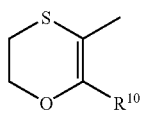
A5

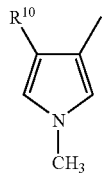
A6

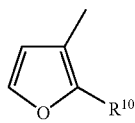
A7

$R^3$ stands for $C_1$-$C_3$-alkyl, $R^4$ stands for hydrogen, halogen, $C_1$-$C_3$-alkyl or $C_1$-$C_3$-halogenalkyl with 1 to 7 fluorine, chlorine and/or bromine atoms, $R^5$ stands for hydrogen, halogen or $C_1$-$C_3$-alkyl, $R^6$ stands for hydrogen, halogen, $C_1$-$C_3$-alkyl, amino, mono- or di($C_1$-$C_3$-alkyl)amino, $R^7$ stands for hydrogen, halogen, $C_1$-$C_3$-alkyl or $C_1$-$C_3$-halogenalkyl with 1 to 7 fluorine, chlorine and/or bromine atoms, $R^8$ stands for halogen, $C_1$-$C_3$-alkyl or $C_1$-$C_3$-halogenalkyl with 1 to 7 fluorine, chlorine and/or bromine atoms, $R^9$ stands for halogen, $C_1$-$C_3$-alkyl or $C_1$-$C_3$-halogenalkyl with 1 to 7 fluorine, chlorine and/or bromine atoms, $R^{10}$ stands for hydrogen, halogen, $C_1$-$C_3$-alkyl or $C_1$-$C_3$-halogenalkyl with 1 to 7 fluorine, chlorine and/or bromine atoms, can be manufactured using Method B, whereby, (1) in a first step, anilides of Formula (II)

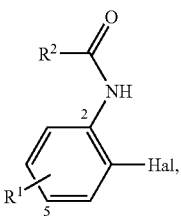
(II)

where Hal, $R^2$ and $R^1$ have the meanings specified above, are reacted with 2-methylbut-3-yn-2-ol of Formula (III)

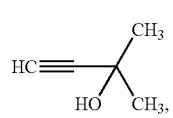
(III)

(2) in a second step, acetone is separated from the thus obtained alkynyl anilides of Formula (IV)

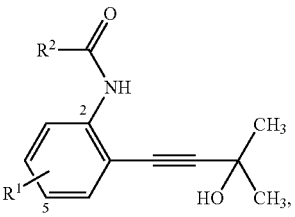
(IV)

where $R^1$ and $R^2$ have the meanings specified above, in the presence of bases, (3) in a third step, the so obtained ethynyl anilides of Formula (V)

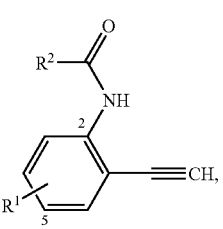
(V)

where $R^1$ and $R^2$ have the meanings specified above, are reacted with thiophene dioxides of Formula (VI)

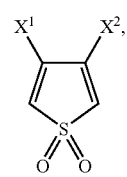
(VI)

where $X^1$ and $X^2$ have the meanings specified above, (4) in a fourth step, the [—C(=O)R²] protective group on the nitrogen is separated from the thus obtained biphenyl amides of Formula (VII)

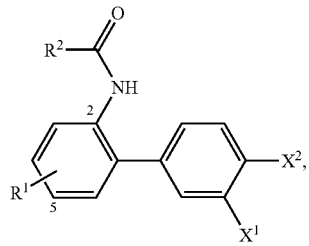

where R¹, R², X¹ and X² have the meanings specified above,
under acidic or basic conditions, and
(5) in a fifth step, the thus obtained biphenyl amines of Formula (I)

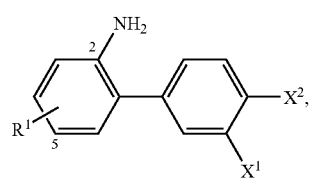

where R¹, X¹ and X² have the meanings specified above, are reacted with carboxylic acid derivatives of Formula (IX)

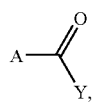

where
A has the meanings specified above and
Y stands for halogen or hydroxy,
in the presence of a catalyst if applicable, in the presence of a condensation agent if applicable, in the presence of an acid binding agent if applicable and in the presence of a diluent if applicable.

If is preferred to perform Method B according to the invention while using initial compounds, in which the indicated moieties each have the following meanings. The preferred, particularly preferred and quite particularly preferred definitions apply to all compounds, in which the respective moieties occur.

Hal, R¹, R², X¹ and X² have the abovementioned preferred, particularly preferred and quite particularly preferred definitions.

A preferably stands for A1, A2, A3, A4 or A5.
A particularly preferably stands for A1 or A2.
R³ preferably stands for methyl.
R⁴ preferably stands for iodine, methyl, difluoromethyl or trifluoromethyl.
R⁴ particularly preferably stands for methyl, difluoromethyl or trifluoromethyl.

R⁵ preferably stands for hydrogen, fluorine, chlorine or methyl.
R⁵ particularly preferably stands for hydrogen or fluorine.
R⁶ preferably stands for hydrogen, chlorine, methyl, amino or dimethylamino.
R⁶ particularly preferably stands for methyl.
R⁷ preferably stands for methyl, difluoromethyl or trifluoromethyl.
R⁸ preferably stands for chlorine, bromine, iodine, methyl, difluoromethyl or trifluoromethyl.
R⁸ particularly preferably stands for iodine, difluoromethyl or trifluoromethyl.
R⁹ preferably stands for bromine or methyl.
R⁹ particularly preferably stands for methyl.
R¹⁰ preferably stands for methyl or trifluoromethyl.
R¹⁰ particularly preferably stands for methyl or trifluoromethyl.
Y preferably stands for chlorine or hydroxy.

The first through fourth steps of Method B correspond to the first through fourth steps of Method A according to the invention and are performed according to the description above.

The carboxylic acid derivatives of Formula (IX), which are to be used as initial compounds for performing the fifth step of Method A according to the invention, are known and/or can be manufactured according to known methods (see WO 03/066609, WO 03/066610, EP-A 0 545 099, EP-A 0 589 301, EP-A 0 589 313 and U.S. Pat. No. 3,547,917).

All inert organic solvents come into consideration as diluents for carrying out the fifth step of Method B according to the invention. Preferred examples are: aliphatic, alicyclic or aromatic hydrocarbons, such as e.g. petroleum ether, hexane, heptane, cyclohexane, methylcyclohexane, benzene, toluene, xylene or decalin; halogenated hydrocarbons, such as e.g. chlorobenzene, dichlorobenzene, dichloro-methane, chloroform, tetrachloromethane, dichloroethane or trichloroethane; ethers, such as diethyl ether, diisopropyl ether, methyl-t-butyl ether, methyl-t-amyl ether, dioxane, tetrahydrofuran, 1,2-dimethoxyethane, 1,2-diethoxyethane or anisole; ketones, such as acetone, butanone, methyl-isobutyl ketone or cyclohexanone; nitriles, such as acetonitrile, propionitrile, n- or i-butyronitrile or benzo-nitrile; amides, such as N,N-dimethylformamide, N,N-dimethylacetamide, N-methylformanilide, N-methylpyrrolidone or hexamethylphosphoric acid triamide; mixtures of these with water or pure water.

The fifth step of Method B according to the invention is carried out in the presence of a suitable acid acceptor, if applicable. All customary inorganic or organic bases come into consideration as such. Preferred examples are: alkaline earth metal- or alkali metal-hydrides, -hydroxides, -amides, -alcoholates, -acetates, -carbonates or -hydrogen carbonates, such as e.g. sodium hydride, sodium amide, lithium diisopropyl amide, sodium methylate, sodium ethylate, potassium-tert.-butylate, sodium hydroxide, potassium hydroxide, sodium acetate, sodium carbonate, potassium carbonate, potassium hydrogen carbonate, sodium hydrogen carbonate or ammonium carbonate, as well as tertiary amines, such as trimethylamine, triethylamine, tributylamine, N,N-dimethylaniline, N,N-dimethyl benzylamine, pyridine, N-methylpiperidine, N-methylmorpholine, N,N-dimethylamino-pyridine, diazabicyclooctane (DABCO), diazabicyclononene (DBN) or diazabicycloundecene (DBU).

The fifth step of Method B according to the invention is performed in the presence of a suitable condensation agent, if applicable. All condensation agents come into consideration, which are customarily used for these types of amidation reactions. The following are mentioned by way of example: acid halide forming agents such as phosgene, phosphorous tribromide, phosphorous trichloride, phosphorous pentachloride, phosphorous oxychloride or thionyl chloride; anhydride forming agents such as chloroformic acid ethyl ester, chloroformic acid methyl ester, chloroformic acid isopropyl ester, chloroformic acid isobutyl ester or methanesulphonyl chloride; carbodiimides, such as N,N'-dicyclohexylcarbodiimide (DCC) or other customary condensation agents, such as phosphorous pentoxide, polyphosphoric acid, N,N'-carbonyldiimideazole, 2-ethoxy-N-ethoxycarbonyl-1,2-dihydro-quinoline (EEDQ), triphenylphosphine/tetrachlorocarbon or bromo-tripyrrolidinophosphonium hexafluorophosphate.

The fifth step of Method B according to the invention is performed in the presence of a catalyst, if applicable. The following are mentioned by way of example: 4-dimethylaminopyridine, 1-hydroxy-benzotriazole or dimethylformamide.

When carrying out the fifth step of Method B according to the invention, the reaction temperatures can be varied within a wide range. Generally, the work is done at temperatures of 0° C. to 150° C., preferably at temperatures of 0° C. to 80° C.

In order carry out the fifth step of Method B according to the invention for the manufacture of the compounds of Formula (VIII), generally 0.8 to 15 Mol, preferably 0.8 to 8 Mol of biphenyl amine of Formula (I) is used per Mol of the carboxylic acid derivative of Formula (IX).

The methods according to the invention for the manufacture of biphenyl amines as well as the manufacture of fungicidally active carboxamides are described in the following examples, which illustrate the descriptions above. However, the examples are not to be interpreted in a restrictive manner.

PREPARATION EXAMPLES

Example 1

Step 1: N-[4-fluoro-2-(3-hydroxy-3-methylbut-1-yn-1-yl)phenyl]acetamide

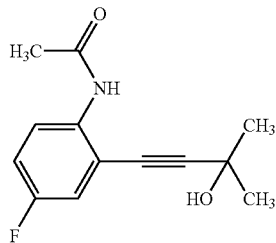

0.32 g (1.2 mmol, purity 99%) triphenylphosphine, 0.085 g (0.12 mmol, purity 99%) bis-triphenylphosphine palladium dichloride, and 0.14 g (0.72 mmol, purity 98%) copper(I) iodide are added to a mixture of 56.8 g (0.24 mol, purity 98%) N-(2-bromo-4-fluorophenyl)acetamide, 30.9 g (0.264 mol, purity 98%) 2-methylbut-3-yn-2-ol and 121.4 g (1.2 mol) triethylamine and the mixture is heated for 6 hours while stirring at 85° C. The surplus triethylamine is distilled off in a vacuum, approximately 170 ml toluene is added, the same quantity of water is added, and the phases are separated at ~70° C.

After cooling to room temperature, 34.4 g of the desired N-[4-fluoro-2-(3-hydroxy-3-methylbut-1-yn-1-yl)phenyl] acetamide crystallizes from the toluene phase as a white solid substance with a purity of 97% (yield: 91% of the theoretical yield).

Solidification point: 120° C.

Step 2: N-(2-ethynyl-4-fluorophenyl)acetamide

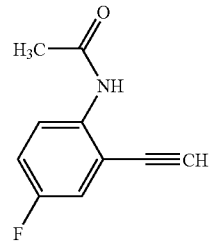

3.2 g (0.018 mol) of a 30% methanol sodium methylate solution is added to a suspension of 21.7 g (0.09 mol, purity 97.7%) N-[4-fluoro-2-(3-hydroxy-3-methylbut-1-yn-1-yl) phenyl]acetamide and 180 ml of dry toluene. The mixture is heated under reflux and approximately 60 ml of distillate is removed over 1 hour. While performing the reaction, the thermal load of the reaction mixture is kept as low as possible (quickly heating, quickly cooling after the reaction is completed), in order to suppress undesired indole formation. The mixture is diluted with toluene, washed three times with water, dried and the solvent is distilled off in a vacuum.

This yields 15.2 g (yield: 76.2% of the theoretical yield) of light-beige crystals of N-(2-ethynyl-4-fluorophenyl)acetamide, which are re-crystallised from xylene.

Melting point: 103° C.

Step 3: N-(3',4'-dichloro-5-fluorobiphenyl-2-yl)acetamide

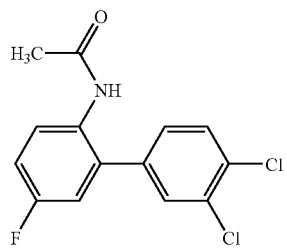

A solution of 6.7 g (0.036 mol) 3,4-dichlorothiophene-1, 1-dioxide in 50 ml of dry toluene is dripped into 5.3 g (0.03 mol) N-(2-ethynyl-4-fluorophenyl)acetamide dissolved in 30 ml of dry xylene over 4 hours while stirring at 130° C. At the same time, toluene is distilled off in such a way that an internal temperature of 130° C. is maintained. The mixture is stirred for 2 hours at 130° C. and the solvent is distilled off in a vacuum. The raw yield amounts to 10.4 g.

After re-crystallisation from xylene, the reaction yields 6.5 g of N-(3',4'-dichloro-5-fluorobiphenyl-2-yl)acetamide (yield: 72.7% of the theoretical yield).

Melting point: 138° C.-140° C.

Alternative:

A solution of 7.3 g (0.0396 mol) 3,4-dichlorothiophene-1, 1-dioxide in 30 ml of dry n-butyronitrile is dripped into 5.8 g (0.033 mol) N-(2-ethynyl-4-fluorophenyl)acetamide dissolved in 30 ml of dry n-butyronitrile over 8 hours while stirring under reflux. The mixture is then stirred for 6 hours under reflux and the solvent is distilled off in a vacuum. The raw yield totals 12.7 g.

After re-crystallisation from xylene, the reaction yields 7.6 g of N-(3',4'-dichloro-5-fluorobiphenyl-2-yl)acetamide (yield: 77.5% of the theoretical yield).

Melting point: 138° C.-140° C.

Step 4: 3',4'-dichloro-5-fluorobiphenyl-2-amine

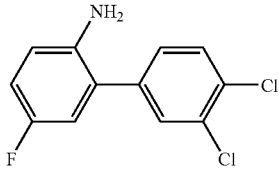

0.08 mol of an approximately 45% aqueous potassium hydroxide solution is added to a suspension of 6.3 g (0.02 mol, purity: 95%) N-(3',4'-dichloro-5-fluorobiphenyl-2-yl) acetamide and 12 ml 2-methoxyethanol. This is heated to 100° C., stirred for 4 hours, cooled and the solvent is distilled off in a vacuum. The residue is mixed with ice water and extracted several times with toluene.

After drying and distilling off the toluene, this yields 4.8 g (yield: 92% of the theoretical yield) 3',4'-dichloro-5-fluorobiphenyl-2-amine as a brown solid substance.

Melting point: 58° C.

Example 2

Step 1: N-[4-fluoro-2-(3-hydroxy-3-methylbut-1-yn-1-yl)phenyl]-2,2-dimethylpropanamide

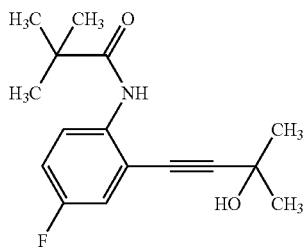

0.12 g (0.45 mmol, purity 99%) triphenylphosphine, 0.032 g (0.045 mmol, purity 99%) bis-triphenylphosphine palladium dichloride and 0.052 g (0.27 mmol, purity 98%) copper (I)iodide are added to a mixture of 25.0 g (0.09 mol, purity 99%) N-(2-bromo-4-fluorophenyl)-2,2-dimethyl-propanamide, 11.6 g (0.135 mol, purity 98%) 2-methylbut-3-yn-2-ol and 45.5 g (0.45 mol) triethylamine, and the mixture is heated 6 hours while stirring at 85° C. The surplus triethylamine is distilled off in a vacuum, and the residue is dissolved in approximately 70 ml toluene, washed three times with 30 ml each time, dried and the solvent is distilled off in a vacuum. The residue is dissolved in acetic acid ethyl ester and filtered over silica gel.

After concentrating the compound in a rotary evaporator, the reaction yields 12.8 g of red oil comprised of 82.8% N-[4-fluoro-2-(3-hydroxy-3-methylbut-1-yn-1-yl)phenyl]-2,2-dimethylpropanamide.

Step 2: N-(2-ethynyl-4-fluorophenyl)-2,2-dimethylpropanamide

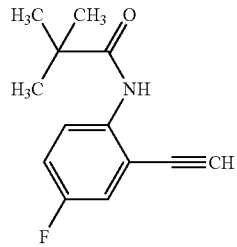

0.54 g (0.003 mol) of a 30% methanol sodium methylate solution is added to a solution of 5.0 g (0.015 mol, purity 82.8%) N-[4-fluoro-2-(3-hydroxy-3-methylbut-1-yn-1-yl) phenyl]-2,2-dimethylpropanamide in 30 ml of dry toluene. The mixture is heated under reflux and approximately 10 ml of distillate is removed over 1 hour. While performing the reaction, the thermal load of the reaction mixture is kept as low as possible (quickly heating, quickly cooling following completion of the reaction), in order to suppress undesired indole formation. The mixture is diluted with 15 ml toluene, washed twice with 20 ml water each time, dried and the solvent is distilled off in a vacuum.

The reaction yields 3.3 g of red oil (yield: 77.5% of the theoretical yield) comprised of 77.3% N-(2-ethynyl-4-fluorophenyl)-2,2-dimethylpropanamide.

Step 3: N-(3',4'-dichloro-5-fluorobiphenyl-2-yl)-2,2-dimethylpropanamide

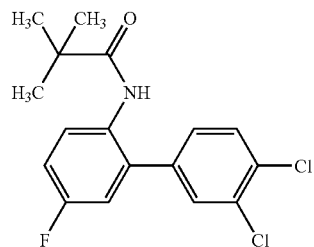

A solution of 2.0 g (0.011 mol) 3,4-dichlorothiophene-1,1-dioxide in 15 ml of dry 2-methoxyethanol is dripped into a solution of 2.6 g (0.009 mol) N-(2-ethynyl-4-fluorophenyl)-2,2-dimethylpropanamide (concentration 77.3%) in 15 ml of dry 2-methoxyethanol over 4 hours while stirring under reflux. The mixture is then stirred for 3 hours at boiling temperature and the solvent is distilled off in a vacuum.

After purification with column chromatography, the reaction yields 2.3 g N-(3',4'-dichloro-5-fluorobiphenyl-2-yl)-2,2-dimethylpropanamide (yield: 74.2% of the theoretical yield).

Melting point: 130° C.-131° C.

Step 4: 3',4'-dichloro-5-fluorobiphenyl-2-amine

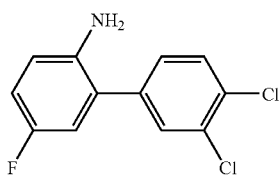

0.024 mol of an approximately 45% aqueous potassium hydroxide solution is added to a suspension of 2.1 g (0.006 mol) N-(3',4'-dichloro-5-fluorobiphenyl-2-yl)-2,2-dimethyl-propanamide and 4 ml 2-methoxyethanol. The mixture is heated to 100° C., stirred for 4 hours, cooled and the solvent is distilled off in a vacuum. The residue is mixed with ice water and extracted several times with toluene.

After drying and distilling off the toluene, the reaction yields 1.4 g (yield: 91% of the theoretical yield) 3',4'-dichloro-5-fluorobiphenyl-2-amine as a brown solid substance.

Melting point: 58° C.

Example 3

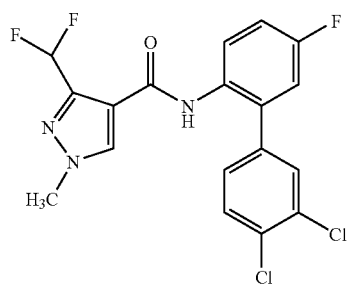

0.333 g (1.3 mmol) 3',4'-dichloro-5-fluorobiphenyl-2-amine and 0.034 g (1.56 mmol) 3-(difluoromethyl)-1-methyl-1H-pyrazole-4-carbonylchloride are dissolved in 6 ml tetrahydrofuran and mixed with 0.36 ml (2.6 mmol) triethylamine. The reaction solution is stirred for 16 hours at 60° C. It is concentrated for analysis and chromatographed with cyclohexane/acetic acid ethyl ester on silica gel.

The reaction yields 0.39 g (72% of the theoretical yield) N-(3',4'-dichloro-5-fluorobiphenyl-2-yl)-3-(difluoromethyl)-1-methyl-1H-pyrazole-4-carboxamide and log P (pH 2.3)=3.33.

The invention claimed is:
1. A method for the manufacture of a biphenyl amine of the general Formula (I)

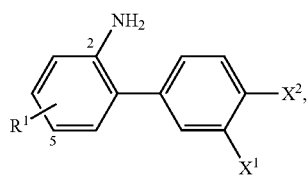

where
$R^1$ stands for hydrogen, fluorine, chlorine, $C_1$-$C_4$-alkyl, $C_1$-$C_4$-alkoxy, $C_1$-$C_4$-alkylthio or $C_1$-$C_4$-halogenalkyl,
$X^1$ stands for fluorine, chlorine or bromine,
$X^2$ stands for fluorine, chlorine or bromine,
comprising,
(1) reacting an anilide of Formula (II) with 2-methylbut-3-yn-2-ol of Formula (III) to obtain an alkynyl anilide of Formula (IV)

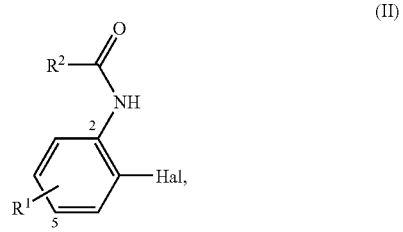

where
Hal stands for chlorine, bromine or iodine,
$R^2$ stands for hydrogen, $C_1$-$C_4$-alkyl or $C_1$-$C_4$-alkoxy, and
$R^1$ stands for hydrogen, fluorine, chlorine, $C_1$-$C_4$-alkyl, $C_1$-$C_4$-alkoxy, $C_1$-$C_4$-alkylthio or $C_1$-$C_4$-halogenalkyl,

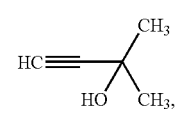

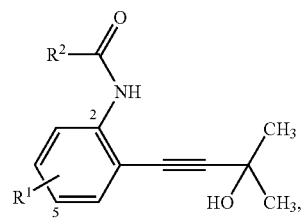

where $R^1$ and $R^2$ have the meanings specified above,
(2) removing an acetone molecule from said alkynyl anilide of Formula (IV) in the presence of a base to form an ethynyl anilide of Formula (V)

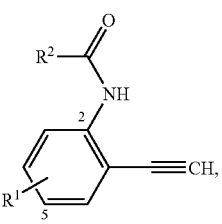

where $R^1$ and $R^2$ have the meanings specified above, (3) reacting said ethynyl anilide of Formula (V) with an thiophene dioxide of Formula (VI) to obtain a biphenyl amide of Formula (VII)

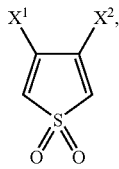
(VI)

where $X^1$ and $X^2$ have the meanings specified above,

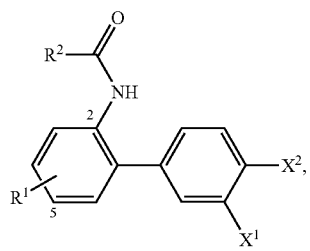
(VII)

where $R^1$, $R^2$, $X^1$ and $X^2$ have the meanings specified above,
and
(4) removing the [—C(=O)R²] protective group from said biphenyl amide of Formula (VII).

2. A method according to claim 1, wherein
$R^1$ stands for hydrogen, fluorine, chlorine, methyl, iso-propyl, trifluoromethyl, methoxy or methylthio, and
$R^2$ stands for hydrogen, methyl, ethyl, iso-propyl, tert-butyl, methoxy, ethoxy, iso-propoxy or tert-butoxy.

3. A method according to claim 1, wherein said anilide of Formula (II) is an anilide of Formula (II-a)

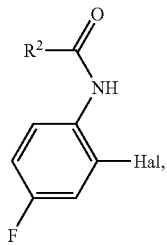
(II-a)

where Hal and $R^2$ have the meanings specified in claim 1.

* * * * *